United States Patent
Pasquier et al.

(10) Patent No.: US 7,517,368 B2
(45) Date of Patent: *Apr. 14, 2009

(54) INDOLYLTHIAZOLIUMAZO DYES-CONTAINING COLORANTS FOR KERATIN FIBERS

(75) Inventors: Cecile Pasquier, Marly (CH); Veronique Buclin, Morlon (CH); Nadia Duc-Reichlin, Lully (CH); Caroline Kiener, Marly (CH); Hans-Juergen Braun, Ueberstorf (CH)

(73) Assignee: Wella AG, Darmstadt (DE)

( * ) Notice: Subject to any disclaimer, the term of this patent is extended or adjusted under 35 U.S.C. 154(b) by 356 days.

This patent is subject to a terminal disclaimer.

(21) Appl. No.: 10/587,061

(22) PCT Filed: Nov. 26, 2004

(86) PCT No.: PCT/EP2004/013401

§ 371 (c)(1),
(2), (4) Date: Jul. 21, 2006

(87) PCT Pub. No.: WO2005/079734

PCT Pub. Date: Sep. 1, 2005

(65) Prior Publication Data

US 2008/0271264 A1    Nov. 6, 2008

(30) Foreign Application Priority Data

Feb. 21, 2004    (DE) .................. 10 2004 008 607

(51) Int. Cl.
*A61Q 5/10* (2006.01)
*C07D 277/00* (2006.01)

(52) U.S. Cl. .............. 8/405; 8/406; 8/408; 8/409; 8/570; 8/571; 8/575; 548/146

(58) Field of Classification Search ............... 8/405, 8/406, 408, 409, 570, 571, 575; 548/146; 534/610, 765
See application file for complete search history.

(56) References Cited

U.S. PATENT DOCUMENTS 4,104,268 A * 8/1978 Dorsch et al. ............... 534/610

FOREIGN PATENT DOCUMENTS

| BE | 768 389 | 11/1971 |
|----|---------|---------|
| CH | 567 074 | 9/1975 |
| DE | 2 114 747 | 10/1971 |

OTHER PUBLICATIONS

STIC Search Report dated Aug. 27, 2008.*

* cited by examiner

*Primary Examiner*—Eisa B Elhilo
(74) *Attorney, Agent, or Firm*—Micahel J. Stricker

(57) ABSTRACT

The present invention has for an object agents for coloring keratin fibers and containing at least one indolylthiazoliumazo dye of general formula (I)

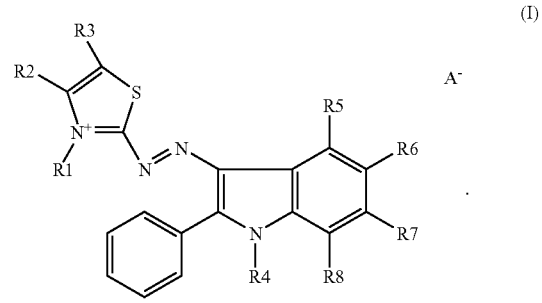

(I)

12 Claims, No Drawings

INDOLYLTHIAZOLIUMAZO DYES-CONTAINING COLORANTS FOR KERATIN FIBERS

CROSS-REFERENCE TO RELATED APPLICATIONS

This applications claims priority under 35U.S.C 119(a)-(d) to German Patent Applications DE 102004008607.9, filed 21 Feb. 2004.

The present invention has for an object agents for coloring keratin fibers, for example wool, furs and hair, and containing indolylthiazoliumazo dyes.

For the color-changing treatment of keratin fibers, two coloring methods are used as a rule. By the first method, the coloring is accomplished with oxidative or permanent colorants by use of a mixture of different developers and couplers as well as an oxidant. By this method, if necessary, it is possible to add a direct (non-oxidative) dye if the coloring result is to be adjusted or special coloring effects are to be achieved. The second method involves the exclusive use of direct dyes which in an appropriate carrier composition are applied to the fibers. This method is easy to apply, very gentle and causes only minor damage to the keratin fibers. The direct dyes used for this purpose are subject to many requirements. For example, they must be unobjectionable in toxicological and dermatological terms and must make it possible to attain colorations of a desired intensity which, among other things, presupposes sufficient water solubility. Moreover, the colorations obtained are required to exhibit good light stability, acid resistance and abrasion resistance.

The advantages of direct coloring over oxidative coloring lie in a generally lower hair damage, because normally the method involves working at lower pH values (below 9) and without an oxidant. Direct dyes are also used in various ways as color shade-adjusting aids. For a direct (non-oxidative) colorant for keratin fibers it is, as a rule, necessary to use a combination of different non-oxidative dyes. Because the selection of dyes that can be used for keratin fibers is limited, a need for such dyes continues to exist.

We have now found that certain indolylthiazoliumazo dyes impart to keratin fibers an intense red to violet color and that they exhibit unusually good light stability and resistance to perspiration.

The present invention therefore has for an object an agent for coloring keratin fibers, particularly human hair, characterized in that it contains at least one indolylthiazoliumazo dye of general formula (I)

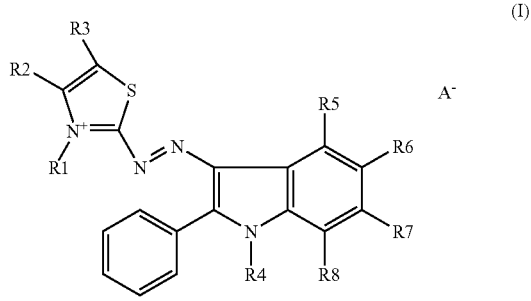

(I)

wherein
R1 is a saturated or unsaturated $(C_1-C_{12})$-alkyl group, a halogen atom (F, Cl, Br, I)-substituted $(C_1-C_{12})$-alkyl group, a hydroxy-$(C_1-C_{12})$-alkyl group, a $(C_1-C_6)$-alkoxy-$(C_1-C_{12})$-alkyl group, an amino-$(C_1-C_{12})$-alkyl group, a $(C_1-C_6)$-alkylamino-$(C_1-C_{12})$-alkyl group, a di-$(C_1-C_6)$-alkylamino-$(C_1-C_{12})$-alkyl group, a cyano-$(C_1-C_{12})$-alkyl group, a substituted or unsubstituted phenyl group or a substituted or unsubstituted benzyl group;

R2 and R3 can be equal or different and independently of each other stand for hydrogen, a halogen atom (F, Cl, Br, I), a saturated or unsaturated $(C_1-C_{12})$-alkyl group, a $(C_1-C_{12})$-alkoxy group, a nitro group, an amino group, a $(C_1-C_{12})$-alkylamino group, a di$(C_1-C_{12})$-alkylamino group, a $(C_1-C_{12})$-hydroxyalkylamino group, a di$(C_1-C_{12})$-hydroxyalkylamino group, a substituted or unsubstituted phenyl group or a substituted or unsubstituted heteroaryl group;

R4 stands for hydrogen, a saturated or unsaturated $(C_1-C_{12})$-alkyl group, a halogen atom (F, Cl, Br, I)-substituted $(C_1-C_{12})$-alkyl group, a hydroxy-$(C_1-C_{12})$-alkyl group, $(C_1-C_6)$-alkoxy-$(C_1-C_{12})$-alkyl group, an amino-$(C_1-C_{12})$-alkyl group, a $(C_1-C_6)$-alkylamino-$(C_1-C_{12})$-alkyl group, a di$(C_1-C_6)$-alkylamino-$(C_1-C_{12})$-alkyl group, a cyano-$(C_1-C_{12})$-alkyl group, a substituted or unsubstituted phenyl group, a substituted or unsubstituted benzyl group or a substituted or unsubstituted heteroaryl group;

R5, R6, R7 and R8 can be equal or different and independently of each other stand for hydrogen, a halogen atom (F, Cl, Br, I), a saturated or unsaturated $(C_1-C_{12})$-alkyl group, a hydroxyl group, a $(C_1-C_{12})$-alkoxy group, a nitro group, an amino group, a $(C_1-C_{12})$-alkyl-amino group or a di$(C_1-C_{12})$-alkylamino group, and A⁻ stands for an anion of an organic or inorganic acid.

Preferred among the afore-indicated compounds of formula (I) are those wherein R1 stands for a saturated or unsaturated $(C_1-C_{12})$-alkyl group and R4 stands for hydrogen, a saturated or unsaturated $(C_1-C_{12})$-alkyl group or a substituted or unsubstituted phenyl group. Particularly preferred are compounds of formula (I) wherein R1 stands for a saturated $(C_1-C_{12})$-alkyl group and R4 stands for hydrogen, a saturated $(C_1-C_{12})$-alkyl group or an unsubstituted phenyl group.

A⁻ is preferably chloride, bromide, iodide, hydrogen sulfate, sulfate, toluenesulfonate, benzenesulfonate, monomethylsulfate, hexafluorophosphate, hexafluoroantimonate, tetrafluoroborate, tetraphenylborate, formate, acetate or propionate, the chloride ion, bromide ion and monomethylsulfate ion being particularly preferred.

Suitable compounds of general formula (I) are, for example:
3-methyl-2-[(1-methyl-2-phenyl-1H-indol-3-yl)azo]thiazolium chloride, 3-methyl-2-[(1-methyl-2-phenyl-1H-indol-3-yl)azo]thiazolium bromide, 3-methyl-2-[(1-methyl-2-phenyl-1H-indol-3-yl)azo]thiazolium monomethylsulfate, 3,4-dimethyl-2-[(1-methyl-2-phenyl-1H-indol-3-yl)azo]thiazolium chloride, 3,4-dimethyl-2-[(1-methyl-2-phenyl-1H-indol-3-yl)azo]thiazolium bromide, 3,4-dimethyl-2-[(1-methyl-2-phenyl-1H-indol-3-yl)azo]thiazolium monomethylsulfate, 3,5-dimethyl-2-[(1-methyl-2-phenyl-1H-indol-3-yl)azo]thiazolium chloride, 3,5-dimethyl-2-[(1-methyl-2-phenyl-1H-indol-3-yl)azo]thiazolium bromide, 3,5-dimethyl-2-[(1-methyl-2-phenyl-1H-indol-3-yl)azo]thiazolium monomethylsulfate, 3,4,5-trimethyl-2-[(1-methyl-2-phenyl-1H-indol-3-yl)azo]thiazolium chloride, 3,4,5-trimethyl-2-[(1-methyl-2-phenyl-1H-indol-3-yl)azo]thiazolium bromide, 3,4,5-trimethyl-2-[(1-methyl-2-phenyl-1H-indol-3-yl)azo]thiazolium monomethylsulfate, 5-bromo-3-methyl-2-[(1-methyl-2-phenyl-1H-indol-3-yl)azo]thiazolium chloride, 5-bromo-3-methyl-2-[(1-methyl-2-phenyl-1H-indol-3-yl)

azo]-thiazolium bromide, 5-bromo-3-methyl-2-[(1-methyl-2-phenyl-1H-indol-3-yl)azo]thiazolium monomethylsulfate, 5-methoxy-3-methyl-2-[(1-methyl-2-phenyl-1H-indol-3-yl)azo]thiazolium chloride, 5-methoxy-3-methyl-2-[(1-methyl-2-phenyl-1H-indol-3-yl)azo] thiazolium bromide, 5-methoxy-3-methyl-2-[(1-methyl-2-phenyl-1H-indol-3-yl)azo]thiazolium monomethylsulfate, 5-diethylamino-3-methyl-2-[(1-methyl-2-phenyl-1H-indol-3-yl)azo]thiazolium chloride, 5-diethylamino-3-methyl-2-[(1-methyl-2-phenyl-1H-indol-3-yl)azo]thiazolium bromide, 5-diethylamino-3-methyl-2-[(1-methyl-2-phenyl-1H-indol-3-yl)azo]thiazolium monomethylsulfate, 3-methyl-2-[(1-methyl-2-phenyl-1H-indol-3-yl)azo]-5-nitrothiazolium chloride, 3-methyl-2-[(1-methyl-2-phenyl-1H-indol-3-yl)azo]-5-nitrothiazolium bromide, 3-methyl-2-[(1-methyl-2-phenyl-1H-indol-3-yl)azo]-5-nitrothiazolium monomethylsulfate, 3-methyl-2-[(2-phenyl-1H-indol-3-yl)azo]thiazolium chloride, 3-methyl-2-[(2-phenyl-1H-indol-3-yl)azo]thiazolium bromide, 3-methyl-2-[(2-phenyl-1H-indol-3-yl)azo]thiazolium monomethylsulfate, 3,4-dimethyl-2-[(2-phenyl-1H-indol-3-yl)azo]thiazolium chloride, 3,4-dimethyl-2-[(2-phenyl-1H-indol-3-yl)azo]thiazolium bromide, 3,4-dimethyl-2-[(2-phenyl-1H-indol-3-yl)azo]thiazolium monomethylsulfate, 3,5-dimethyl-2-[(2-phenyl-1H-indol-3-yl)azo]thiazolium chloride, 3,5-dimethyl-2-[(2-phenyl-1H-indol-3-yl)azo]thiazolium bromide, 3,5-dimethyl-2-[(2-phenyl-1H-indol-3-yl)azo]thiazolium monomethylsulfate, 3,4,5-trimethyl-2-[(2-phenyl-1H-indol-3-yl)azo]thiazolium chloride, 3,4,5-trimethyl-2-[(2-phenyl-1H-indol-3-yl)azo]thiazolium bromide, 3,4,5-trimethyl-2-[(2-phenyl-1H-indol-3-yl)azo]thiazolium monomethylsulfate, 5-bromo-3-methyl-2-[(2-phenyl-1H-indol-3-yl)azo]thiazolium chloride, 5-bromo-3-methyl-2-[(2-phenyl-1H-indol-3-yl)azo]thiazolium bromide, 5-bromo-3-methyl-2-[(2-phenyl-1H-indol-3-yl)azo]thiazolium monomethylsulfate, 5-methoxy-3-methyl-2-[(2-phenyl-1H-indol-3-yl)azo]thiazolium chloride, 5-methoxy-3-methyl-2-[(2-phenyl-1H-indol-3-yl)azo]thiazolium bromide, 5-methoxy-3-methyl-2-[(2-phenyl-1H-indol-3-yl)azo]thiazolium monomethylsulfate, 5-diethylamino-3-methyl-2-[(2-phenyl-1H-indol-3-yl)azo]thiazolium chloride, 5-diethylamino-3-methyl-2-[(2-phenyl-1H-indol-3-yl)azo]thiazolium bromide, 5-diethylamino-3-methyl-2-[(2-phenyl-1H-indol-3-yl)azo]thiazolium monomethylsulfate, 3-methyl-5-nitro-2-[(2-phenyl-1H-indol-3-yl)azo]thiazolium chloride, 3-methyl-5-nitro-2-[(2-phenyl-1H-indol-3-yl)azo]thiazolium bromide, 3-methyl-5-nitro-2-[(2-phenyl-1H-indol-3-yl)azo]thiazolium monomethylsulfate, 2-[(1-ethyl-2-phenyl-1H-indol-3-yl)azo]-3-methylthiazolium chloride, 2-[(1-ethyl-2-phenyl-1H-indol-3-yl)azo]-3-methylthiazolium bromide, 2-[(1-ethyl-2-phenyl-1H-indol-3-yl)azo]-3-methylthiazolium monomethylsulfate, 2-[(1-ethyl-2-phenyl-1H-indol-3-yl)-azo]-3,4-dimethylthiazolium chloride, 2-[(1-ethyl-2-phenyl-1H-indol-3-yl)azo]-3,4-dimethylthiazolium bromide, 2-[(1-ethyl-2-phenyl-1H-indol-3-yl)azo]-3,4-dimethylthiazolium monomethylsulfate, 2-[(1-ethyl-2-phenyl-1H-indol-3-yl)azo]-3,5-dimethylthiazolium chloride, 2-[(1-ethyl-2-phenyl-1H-indol-3-yl)azo]-3,5-dimethylthiazolium bromide, 2-[(1-ethyl-2-phenyl-1H-indol-3-yl)azo]-3,5-dimethylthiazolium monomethylsulfate, 2-[(1-ethyl-2-phenyl-1H-indol-3-yl)azo]-3,4,5-trimethylthiazolium chloride, 2-[(1-ethyl-2-phenyl-1H-indol-3-yl)azo]-3,4,5-trimethylthiazolium bromide, 2-[(1-ethyl-2-phenyl-1H-indol-3-yl)azo]-3,4,5-trimethylthiazolium monomethylsulfate, 5-bromo-2-[(1-ethyl-2-phenyl-1H-indol-3-yl)azo]-3-methyl-thiazolium chloride, 5-bromo-2-[(1-ethyl-2-phenyl-1H-indol-3-yl)azo]-3-methylthiazolium bromide, 5-bromo-2-[(1-ethyl-2-phenyl-1H-indol-3-yl)azo]-3-methylthiazolium monomethylsulfate, 2-[(1-ethyl-2-phenyl-1H-indol-3-yl)azo]-5-methoxy-3-methylthiazolium chloride, 2-[(1-ethyl-2-phenyl-1H-indol-3-yl)azo]-5-methoxy-3-methylthiazolium bromide, 2-[(1-ethyl-2-phenyl-1H-indol-3-yl)azo]-5-methoxy-3-methylthiazolium monomethylsulfate, 5-diethyl-amino-2-[(1-ethyl-2-phenyl-1H-indol-3-yl)azo]-3-methylthiazolium chloride, 5-diethylamino-2-[(1-ethyl-2-phenyl-1H-indol-3-yl)azo]-3-methylthiazolium bromide, 5-diethylamino-2-[(1-ethyl-2-phenyl-1H-indol-3-yl)azo]-3-methylthiazolium monomethylsulfate, 2-[(1-ethyl-2-phenyl-1H-indol-3-yl)azo]-3-methyl-5-nitrothiazolium chloride, 2-[(1-ethyl-2-phenyl-1H-indol-3-yl)azo]-3-methyl-5-nitrothiazolium bromide, 2-[(1-ethyl-2-phenyl-1H-indol-3-yl)azo]-3-methyl-5-nitrothiazolium monomethylsulfate, 3-methyl-2-[(1,2-diphenyl-1H-indol-3-yl)-azo]thiazolium chloride, 3-methyl-2-[(1,2-diphenyl-1H-indol-3-yl)azo]thiazolium bromide, 3-methyl-2-[(1,2-diphenyl-1H-indol-3-yl)azo]thiazolium monomethylsulfate, 3,4-dimethyl-2-[(1,2-diphenyl-1H-indol-3-yl)azo]thiazolium chloride, 3,4-dimethyl-2-[(1,2-diphenyl-1H-indol-3-yl)azo]thiazolium bromide, 3,4-dimethyl-2-[(1,2-diphenyl-1H-indol-3-yl)azo]thiazolium monomethylsulfate, 3,5-dimethyl-2-[(1,2-diphenyl-1H-indol-3-yl)azo]thiazolium chloride, 3,5-dimethyl-2-[(1,2-diphenyl-1H-indol-3-yl)azo]thiazolium bromide, 3,5-dimethyl-2-[(1,2-diphenyl-1H-indol-3-yl)azo]thiazolium monomethylsulfate, 3,4,5-trimethyl-2-[(1,2-diphenyl-1H-indol-3-yl)azo]thiazolium chloride, 3,4,5-trimethyl-2-[(1,2-diphenyl-1H-indol-3-yl)azo]thiazolium bromide, 3,4,5-trimethyl-2-[(1,2-diphenyl-1H-indol-3-yl)azo]thiazolium monomethylsulfate, 5-bromo-3-methyl-2-[(1,2-diphenyl-1H-indol-3-yl)azo]thiazolium chloride, 5-bromo-3-methyl-2-[(1,2-diphenyl-1H-indol-3-yl)azo]thiazolium bromide, 5-bromo-3-methyl-2-[(1,2-diphenyl-1H-indol-3-yl)azo]thiazolium monomethylsulfate, 5-methoxy-3-methyl-2-[(1,2-diphenyl-1H-indol-3-yl)azo]thiazolium chloride, 5-methoxy-3-methyl-2-[(1,2-diphenyl-1H-indol-3-yl)azo]thiazolium bromide, 5-methoxy-3-methyl-2-[(1,2-diphenyl-1H-indol-3-yl)azo]thiazolium monomethylsulfate, 5-diethylamino-3-methyl-2-[(1,2-diphenyl-1H-indol-3-yl)azo]thiazolium chloride, 5-diethylamino-3-methyl-2-[(1,2-diphenyl-1H-indol-3-yl)azo]thiazolium bromide, 5-diethylamino-3-methyl-2-[(1,2-diphenyl-1H-indol-3-yl)azo]-thiazolium monomethylsulfate, 3-methyl-5-nitro-2-[(1,2-diphenyl-1H-indol-3-yl)azo]thiazolium chloride, 3-methyl-5-nitro-2-[(1,2-diphenyl-1H-indol-3-yl)azo] thiazolium bromide, 3-methyl-5-nitro-2-[(1,2-diphenyl-1H-indol-3-yl)azo]thiazolium monomethylsulfate, 3-ethyl-2-[(1-ethyl-2-phenyl-1H-indol-3-yl)azo]thiazolium chloride, 3-ethyl-2-[(1-ethyl-2-phenyl-1H-indol-3-yl)azo]thiazolium bromide, 3-ethyl-2-[(1-ethyl-2-phenyl-1H-indol-3-yl)azo]thiazolium monomethylsulfate, 3-ethyl-2-[(1-ethyl-2-phenyl-1H-indol-3-yl)azo]-4-methylthiazolium chloride, 3-ethyl-2-[(1-ethyl-2-phenyl-1H-indol-3-yl)azo]-4-methylthiazolium bromide, 3-ethyl-2-[(1-ethyl-2-phenyl-1H-indol-3-yl)azo]-4-methylthiazolium monomethylsulfate, 3-ethyl-2-[(1-ethyl-2-phenyl-1H-indol-3-yl)azo]-5-methylthiazolium chloride, 3-ethyl-2-[(1-ethyl-2-phenyl-1H-indol-3-yl)azo]-5-methylthiazolium bromide, 3-ethyl-2-[(1-ethyl-2-phenyl-1H-indol-3-yl)azo]-5-methylthiazolium monomethylsulfate, 3-ethyl-2-[(1-ethyl-2-phenyl-1H-indol-3-yl)

azo]-4,5-dimethylthiazolium chloride, 3-ethyl-2-[(1-ethyl-2-phenyl-1H-indol-3-yl)azo]-4,5-dimethylthiazolium bromide, 3-ethyl-2-[(1-ethyl-2-phenyl-1H-indol-3-yl)azo]-4,5-dimethylthiazolium monomethylsulfate, 5-bromo-3-ethyl-2-[(1-ethyl-2-phenyl-1H-indol-3-yl)azo]thiazolium chloride, 5-bromo-3-ethyl-2-[(1-ethyl-2-phenyl-1H-indol-3-yl)-azo]thiazolium bromide, 5-bromo-3-ethyl-2-[(1-ethyl-2-phenyl-1H-indol-3-yl)azo]thiazolium monomethylsulfate, 3-ethyl-2-[(1-ethyl-2-phenyl-1H-indol-3-yl)azo]-5-methoxythiazolium chloride, 3-ethyl-2-[(1-ethyl-2-phenyl-1H-indol-3-yl)azo]-5-methoxythiazolium bromide, 3-ethyl-2-[(1-ethyl-2-phenyl-1H-indol-3-yl)azo]-5-methoxythiazolium monomethylsulfate, 3-ethyl-5-diethylamino-2-[(1-ethyl-2-phenyl-1H-indol-3-yl)azo]thiazolium chloride, 3-ethyl-5-diethyl-amino-2-[(1-ethyl-2-phenyl-1H-indol-3-yl)azo]thiazolium bromide, 3-ethyl-5-diethyl-amino-2-[(1-ethyl-2-phenyl-1H-indol-3-yl)azo]thiazolium monomethylsulfate, 3-ethyl-2-[(1-methyl-2-phenyl-1H-indol-3-yl)azo]thiazolium chloride, 3-ethyl-2-[(1-methyl-2-phenyl-1H-indol-3-yl)azo]thiazolium bromide, 3-ethyl-2-[(1-methyl-2-phenyl-1H-indol-3-yl)azo]thiazolium, monomethylsulfate, 2-[(1-methyl-2-phenyl-1H-indol-3-yl)azo]-3-propylthiazolium chloride, 2-[(1-methyl-2-phenyl-1H-indol-3-yl)azo]-3-propylthiazolium bromide, 2-[(1-methyl-2-phenyl-1H-indol-3-yl)azo]-3-propylthiazolium monomethylsulfate, 3-hydroxyethyl-2-[(1-methyl-2-phenyl-1H-indol-3-yl)azo]thiazolium chloride, 3-hydroxyethyl-2-[(1-methyl-2-phenyl-1H-indol-3-yl)azo]thiazolium bromide, 3-hydroxyethyl-2-[(1-methyl-2-phenyl-1H-indol-3-yl)azo]thiazolium monomethylsulfate, 2-[(1-methyl-2-phenyl-1H-indol-3-yl)azo]-3-(2-propenyl)thiazolium chloride, 2-[(1-methyl-2-phenyl-1H-indol-3-yl)azo]-3-(2-propenyl)thiazolium bromide and 2-[(1-methyl-2-phenyl-1H-indol-3-yl)azo]-3-(2-propenyl)thiazolium monomethylsulfate.

Particularly preferred compounds of formula (I) are 3-methyl-2-[(1-methyl-2-phenyl-1H-indol-3-yl)azo]thiazolium chloride, 3-methyl-2-[(1-methyl-2-phenyl-1H-indol-3-yl)azo]thiazolium bromide, 3-methyl-2-[(1-methyl-2-phenyl-1H-indol-3-yl)azo]thiazolium monomethylsulfate, 3,4-dimethyl-2-[(1-methyl-2-phenyl-1H-indol-3-yl)azo]thiazolium chloride, 3,4-dimethyl-2-[(1-methyl-2-phenyl-1H-indol-3-yl)azo]thiazolium bromide, 3,4-dimethyl-2-[(1-methyl-2-phenyl-1H-indol-3-yl)azo]thiazolium monomethylsulfate, 3,5-dimethyl-2-[(1-methyl-2-phenyl-1H-indol-3-yl)azo]thiazolium chloride, 3,5-dimethyl-2-[(1-methyl-2-phenyl-1H-indol-3-yl)azo]thiazolium bromide, 3,5-dimethyl-2-[(1-methyl-2-phenyl-1H-indol-3-yl)azo]thiazolium monomethylsulfate, 3,4,5-trimethyl-2-[(1-methyl-2-phenyl-1H-indol-3-yl)azo]thiazolium chloride, 3,4,5-trimethyl-2-[(1-methyl-2-phenyl-1H-indol-3-yl)azo]thiazolium bromide, 3,4,5-trimethyl-2-[(1-methyl-2-phenyl-1H-indol-3-yl)azo]thiazolium monomethylsulfate, 5-bromo-3-methyl-2-[(1-methyl-2-phenyl-1H-indol-3-yl)azo]thiazolium chloride, 5-bromo-3-methyl-2-[(1-methyl-2-phenyl-1H-indol-3-yl)azo]-thiazolium bromide, 5-bromo-3-methyl-2-[(1-methyl-2-phenyl-1H-indol-3-yl)azo]thiazolium monomethylsulfate, 5-methoxy-3-methyl-2-[(1-methyl-2-phenyl-1H-indol-3-yl)azo]thiazolium chloride, 5-methoxy-3-methyl-2-[(1-methyl-2-phenyl-1H-indol-3-yl)azo]thiazolium bromide, 5-methoxy-3-methyl-2-[(1-methyl-2-phenyl-1H-indol-3-yl)azo]thiazolium monomethylsulfate, 3-methyl-2-[(2-phenyl-1H-indol-3-yl)azo]thiazolium chloride, 3-methyl-2-[(2-phenyl-1H-indol-3-yl)azo]thiazolium bromide, 3-methyl-2-[(2-phenyl-1H-indol-3-yl)azo]thiazolium monomethylsulfate, 3,4-dimethyl-2-[(2-phenyl-1H-indol-3-yl)azo]thiazolium chloride, 3,4-dimethyl-2-[(2-phenyl-1H-indol-3-yl)azo]thiazolium bromide, 3,4-dimethyl-2-[(2-phenyl-1H-indol-3-yl)azo]thiazolium monomethylsulfate, 3,5-dimethyl-2-[(2-phenyl-1H-indol-3-yl)azo]thiazolium chloride, 3,5-dimethyl-2-[(2-phenyl-1H-indol-3-yl)azo]thiazolium bromide, 3,5-dimethyl-2-[(2-phenyl-1H-indol-3-yl)azo]thiazolium monomethylsulfate, 3,4,5-trimethyl-2-[(2-phenyl-1H-indol-3-yl)azo]thiazolium chloride, 3,4,5-trimethyl-2-[(2-phenyl-1H-indol-3-yl)azo]thiazolium bromide, 3,4,5-trimethyl-2-[(2-phenyl-1H-indol-3-yl)azo]thiazolium monomethylsulfate, 5-bromo-3-methyl-2-[(2-phenyl-1H-indol-3-yl)azo]thiazolium chloride, 5-bromo-3-methyl-2-[(2-phenyl-1H-indol-3-yl)azo]thiazolium bromide, 5-bromo-3-methyl-2-[(2-phenyl-1H-indol-3-yl)azo]thiazolium monomethylsulfate, 5-methoxy-3-methyl-2-[(2-phenyl-1H-indol-3-yl)azo]thiazolium chloride, 5-methoxy-3-methyl-2-[(2-phenyl-1H-indol-3-yl)azo]thiazolium bromide, 5-methoxy-3-methyl-2-[(2-phenyl-1H-indol-3-yl)azo]thiazolium monomethylsulfate, 3-methyl-2-[(1,2-diphenyl-1H-indol-3-yl)azo]thiazolium chloride, 3-methyl-2-[(1,2-diphenyl-1H-indol-3-yl)azo]thiazolium bromide, 3-methyl-2-[(1,2-diphenyl-1H-indol-3-yl)azo]thiazolium monomethylsulfate, 3,4-dimethyl-2-[(1,2-diphenyl-1H-indol-3-yl)azo]thiazolium chloride, 3,4-dimethyl-2-[(1,2-diphenyl-1H-indol-3-yl)-azo]thiazolium bromide, 3,4-dimethyl-2-[(1,2-diphenyl-1H-indol-3-yl)azo]thiazolium monomethylsulfate, 3,5-dimethyl-2-[(1,2-diphenyl-1H-indol-3-yl)azo]thiazolium chloride, 3,5-dimethyl-2-[(1,2-diphenyl-1H-indol-3-yl)azo]thiazolium bromide, 3,5-dimethyl-2-[(1,2-diphenyl-1H-indol-3-yl)azo]thiazolium monomethylsulfate, 3,4,5-trimethyl-2-[(1,2-diphenyl-1H-indol-3-yl)-azo]thiazolium chloride, 3,4,5-trimethyl-2-[(1,2-diphenyl-1H-indol-3-yl)azo]thiazolium bromide, 3,4,5-trimethyl-2-[(1,2-diphenyl-1H-indol-3-yl)azo]thiazolium monomethylsulfate, 5-bromo-3-methyl-2-[(1,2-diphenyl-1H-indol-3-yl)azo]thiazolium chloride, 5-bromo-3-methyl-2-[(1,2-diphenyl-1H-indol-3-yl)azo]thiazolium bromide, 5-bromo-3-methyl-2-[(1,2-diphenyl-1H-indol-3-yl)azo]thiazolium monomethylsulfate, 5-methoxy-3-methyl-2-[(1,2-diphenyl-1H-indol-3-yl)azo]thiazolium chloride, 5-methoxy-3-methyl-2-[(1,2-diphenyl-1H-indol-3-yl)-azo]thiazolium bromide and 5-methoxy-3-methyl-2-[(1,2-diphenyl-1H-indol-3-yl)-azo]thiazolium monomethylsulfate.

The colorant of the invention contains the compounds of formula (I) preferably in an amount from 0.01 to 10 weight percent and particularly from 0.1 to 8 weight percent.

Besides the dyes of formula (I), the colorant of the invention can additionally contain other known direct dyes from the group consisting of nitro dyes, azo dyes, anthraquinone dyes and triphenylmethane dyes alone or in admixture with one another, for example 1,4-bis-[(2-hydroxyethyl)amino]-2-nitrobenzene, 1-(2-hydroxyethyl)amino-2-nitro-4-[di(2-hydroxyxyethyl)amino]benzene (HC Blue No. 2), 1-amino-3-methyl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyethyl)amino]-1-[(2-methoxyethyl)amino]-2-nitrobenzene (HC Blue No. 11), 1-[(2,3-dihydroxypropyl)amino]-4-[methyl-(2-hydroxyethyl)amino]-2-nitrobenzene (HC Blue No. 10), 1-[(2,3-dihydroxypropyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylamino-4-[methyl-(2,3-dihydroxypropyl)amino]-2-nitrobenzene (HC Blue No. 6), 2-[(4-amino-2-nitrophenyl)amino]-5-dimethylaminobenzoic acid (HC Blue No. 13), 1-(2-aminoethylamino)$_4$-[di(2-hydroxyethyl)amino]-2-nitrobenzene, 4-[d][2-hydroxyethyl)amino]-2-nitro-1-phenylaminobenzene, 1-amino-4-[(2-hydroxyethyl)amino]-2-nitrobenzene (HC Red No. 7), 2-amino-4,6-dinitrophenol, 1,4-diamino-2-nitrobenzene (C.I. 76070), 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)amino]-2-nitrobenzene (HC Red No. 3), 4-[(2-hydroxyethyl)methylamino]-1-(methylamino)-2-nitrobenzene, 1-amino-4-[(2,3-dihydroxypropyl)amino]-5-methyl-2-nitrobenzene, 1-amino-4-(methylamino)-2-nitrobenzene, 4-amino-2-nitro-1-[(prop-2-en-1-yl)amino]benzene, 4-amino-3-nitrophenol, 4-[(2-hydroxyethyl)-amino]-3-nitrophenol, 4-[(2-nitrophenyl)amino]phenol (HC Orange No. 1), 1-[(2-amino-ethyl)amino]-4-(2-hydroxyethoxy)-2-nitrobenzene (HC Orange No. 2), 4-(2,3-dihydroxy-propoxy)-1-[(2-hydroxyethyl)amino]-2-nitrobenzene (HC Orange No. 3), 1-amino-5-chloro-4-[(2,3-dihydroxypropyl)amino]-2-nitrobenzene (HC Red No. 10), 5-chloro-1,4-[di-(2,3-dihydroxypropyl)amino]-2-nitrobenzene (HC Red No. 11), 2-[(2-hydroxyethyl)-amino]-4,6-dinitrophenol, 4-ethylamino-3-nitrobenzoic acid, 2-[(4-amino-2-nitrophenyl)-amino]benzoic acid, 2-chloro-6-ethylamino-4-nitrophenol, 2-amino-6-chloro-4-nitrophenol, 4-[(3-hydroxypropyl)amino]-3-nitrophenol, 2,5-diamino-6-nitropyridine, 6-amino-3-[(2-hydroxyethyl)amino]-2-nitropyridine, 3-amino-6-[(2-hydroxyethyl)amino]-2-nitropyridine, 3-amino-6-(ethylamino)-2-nitropyridine, 3-[(2-hydroxyethyl)amino]-6-(methylamino)-2-nitropyridine, 3-amino-6-(methylamino)-2-nitropyridine, 6-(ethylamino)-3-[(2-hydroxyethyl)amino]-2-nitropyridine, 1,2,3,4-tetrahydro-6-nitroquinoxaline, 7-amino-3,4-dihydro-6-nitro-2H-1,4-benzoxazine (HC Red No. 14), 1,2-diamino-4-nitrobenzene (C.I. 76020), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[di(2-hydroxyethyl)amino]-5-nitrophenol, 2-[(2-hydroxyethyl)-amino]-1-methoxy-5-nitrobenzene, 2-amino-3-nitrophenol, 1-amino-2-methyl-6-nitrobenzene, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. 6), 1-chloro-2,4-bis[(2-amino]-5-nitrobenzene (HC Yellow No. 10), 1-amino-4-[(2-aminoethyl)amino]-5-methyl-2-nitrobenzene, 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)-amino]-3-nitrobenzamide (HC Yellow No. 15), 3-[(2-hydroxyethyl)amino]-4-methyl-1-nitrobenzene, 4-chloro-3-[(2-hydroxyethyl)-amino]-1-nitrobenzene, 2,4-dinitro-1-hydroxynaphthalene, 1,4-di[(2,3-dihydroxypropyl)-amino]-9,10-anthraquinone, 1,4-di[(2-hydroxyethyl)-amino]-9,10-anthraquinone (C.I. 61545, Disperse Blue 23), 1-[(2-hydroxyethyl)amino]-4-methylamino-9,10-anthraquinone (C.I. 61505, Disperse Blue No. 3), 2-[(2-aminoethyl)-amino]-9,10-anthraquinone (HC Orange No. 5), 1-amino-4-hydroxy-9,10-anthraquinone (C.I. 60710, Disperse Red 15), 1-hydroxy-4-[(4-methyl-2-sulfophenyl)amino]-9,10-anthraquinone, 7-beta-D-glucopyranosyl-9,10-dihydro-1-methyl-9,10-diketo-3,5,6,8-tetrahydroxy-2-anthracenecarboxylic acid (C.I. 75470, Natural Red 4), 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (C.I. 62015, Disperse Red No. 11, Solvent Violet No. 26), 1,4-dihydroxy-5,8-bis[(2-hydroxyethyl)amino]-9,10-anthraquinone (C.I. 62500, Disperse Blue No. 7, Solvent Blue No. 69), 1,4-diamino-9,10-anthraquinone (C.I. 61100, Disperse Violet No. 1), 1-amino-4-(methylamino)-9,10-anthraquinone (C.I. 61105, Disperse Violet No. 4, Solvent Violet No. 12), 2-hydroxy-3-methoxy-1,4-naphthoquinone, 2,5-dihydroxy-1,4-naphthoquinone, 2-hydroxy-3-methyl-1,4-naphthoquinone, 2,5-dihydroxy-1,4-naphthoquinone, 2-hydroxy-3-mathyl-1,4-naphthoquinone, N-{6-[(3-chloro-4-(methylamino)phenyl]imino}-4-methyl-3-keto-1,4-cyclohexadien-1-yl)urea (HC Red No. 9), 2-((4-(di(2-hydroxethyl)amino)phenyl)amino)-5-[(2-hydroxyethyl)amino]-2,5-cyclohexadiene-1,4-dione (HC Green No. 1), 5-hydroxy-1,4-naphthoquinone (C.I. 75500, Natural Brown No. 7), 2-hydroxy-1,4-naphthoquinone (C.I. 75480, Natural Orange No. 6), 1,2-dihydro-2-(1,3-dihydroxy-3-keto-2H-indol-2-ylidene)-3H-indol-3-one C.I. 73000), 1,3-bis(dicyanomethylene)indane, 9-(dimethylamino)benzo[a]-phenoxazin-7-ium chloride (C.I. 51175; Basic Blue No. 6), di[4-(diethylamino)phenyl][4-(ethylamino)naphthyl]carbenium chloride (C.I. 42595; Basic Blue No. 7), di(4-dimethylamino)phenyl)-[4-(methylphenylamino)naphthalen-1-yl]carbenium chloride (C.I. 42563; Basic Blue No. 8), 3,7-di(dimethylamino)phenothiazin-5-ium chloride (C.I. 52015; Basic Blue No. 9), di[4-(dimethylamino)phenyl][4-(phenylamino)naphthyl]carbenium chloride (C.I. 44045; Basic Blue No. 26), 2-[(4-(ethyl(2-hydroxyethyl)amino)phenyl)azo]-6-methoxy-3-methylbenzothiazolium methylsulfate (C.I. 11154; Basic Blue No. 41); Basic Blue No. 77, 8-amino-2-bromo-5-hydroxy-4-imino-6-{[3-(trimethylammonio)phenyl]amino}-1(4H)-naphthalenone chloride (C.I. 56059; Basic Blue No. 99), bis[4-(dimethylamino)phenyl][4-(methylamino)phenyl]carbenium chloride (C.I. 42535; Basic Violet No. 1), tri(4-amino-3-methylphenyl)carbenium chloride (C.I. 42520; Basic Violet No. 2), tris[4-(dimethylamino)phenylamino]carbenium chloride (C.I. 42555; Basic Violet No. 3), 2-[3,6-(diethylamino)dibenzopyranium-9-yl]benzoyl chloride (C.I. 45170; Basic Violet No. 10), di(4-aminophenyl)(4-amino-3-methylphenyl)carbenium chloride (C.I. 42510; Basic Violet No. 14), 1,3-bis[(2,4-diamino-5-methylphenyl)azo]-3-methylbenzene (C.I. 21010; Basic Brown No. 4), 1-[(4-aminophenyl)azo]-7-(trimethylammonio)-2-naphthyl chloride (C.I. 12250; Basic Brown No. 16), 3-[(4-amino-2,5-dimethoxyphenyl)azo]-N.N.N-trimethylbenzenaminium chloride (C.I. 112605; Basic Orange No. 69), 1-[(4-amino-2-nitrophenyl)azo]-7-(trimethylammonio)-2-naphthol chloride (Basic Brown No. 17), 1-[(4-amino-3-nitrophenyl)azo]-7-(trimethylammonio)-2-naphthol chloride (C.I. 12251; Basic Brown No. 17) [sic], 2-[(4-aminophenyl)azo]-1,3-dimethyl-1H-imidazol-3-ium chloride (Basic Orange No. 31), 3,7-diamino-2,8-dimethyl-5-phenylphenazinium chloride (C.I. 50240; Basic Red No. 2), 1,4-dimethyl-5{[4-(dimethylamino)phenyl]azo}-1,2,4-triazolium chloride (C.I. 11055; Basic Red No. 22), 1,3-dimethyl-2-[(4-dimethylamino)phenyl]azo-1H-imidazol-3-ium chloride (Basic Red No. 51), 2-hydroxy-1-[(2-methoxyphenyl)azo]-7-(trimethylammonio)-naphthalene chloride (C.I. 12245; Basic Red No. 76), 2-{2-[(2,4-dimethoxyphenyl)-amino]ethenyl}-1,3,3-trimethyl-3H-indol-1-ium chloride (C.I. 48055; Basic Yellow No. 11), 3-methyl-1-phenyl-4-[(3-(trimethylammonio)phenyl]azo}pyrazol-5-one chloride (C.I. 12719; Basic Yellow No. 57), di[4-(dimethylamino)phenyl]iminomethane hydrochloride (C.I. 41000; Basic Yellow No. 2), 1-methyl-4-[(methylphenylhydrazono)methyl]pyridinium methylsulfate (Basic Yellow No. 87), bis[4-((diethylamino)phenyl] phenylcarbenium hydrogen sulfate (1:1) (C.I. 42040; Basic Green No. 1), di[4-(dimethylamino)phenyl]phenylmethanol (C.I. 42000; Basic Green No. 4), 1-(2-morpholiniumpropylamino)-4-hydroxy-9,10-anthraquinone methylsulfate, 1-{[3-(dimethylpropylaminium)propyl]amino}-4-(methylamino)-9,10-anthraquinone chloride, 1-di[(2-hydroxyethyl) amino]-3-methyl-4-[(4-nitrophenyl)azo]-benzene (C.I. 11210; Disperse Red No. 17), 1-[di(2-hydroxyethyl)amino]-4-[(4-nitrophenyl)azo]benzene (Disperse Black No. 9), 4-[(4-aminonophenyl)azo]-1-[di(2-hydroxy-ethyl)amino]-3-methylbenzene (HC Yellow No. 7), 2,6-diamino-3-[(pyridin-3-yl)-azo]pyridine, 2{[4-(acetylamino)phenyl]azo}-4-methylphenol (C.I. 11855; Disperse Yellow No. 3), 2{[4-(ethyl(2-hydroxyethyl)amino)-2-methylphenyl]azo}-5-nitro-1,3-thiazole (C.I. 111935; Disperse Blue No. 106), 6-hydroxy-5-[(4-sulfophenyl)azo]-2-naphthalenesulfonic acid disodium salt (C.I. 15985; Food Yellow No. 3; FD&C Yellow No. 6), 2,4-dinitro-1-naphthol-7-sulfonic acid disodium salt (C.I. 10316; Acid Yellow No. 1; Food Yellow No. 1), 2-(indan-1,3-dion-2-yl)quinoline-x,x-sulfonic acid (mixture of mono- and disulfonic aid) (C.I. 47005; D&C Yellow No. 10; Food Yellow No. 13; Acid Yellow No. 3), 5-hydroxy-1-(4-sulfophenyl)-4-[(4-sulfophenyl)azo]pyrazole-3-carboxylic acid trisodium salt (C.I. 19140; Food Yellow No. 4; Acid Yellow No. 23), 9-(2-carboxyphenyl-6-hydroxy-3H-xanthen-3-one (C.I. 45350; Acid Yellow No. 73; D&C Yellow No. 8), 4-[(4-amino-3-sul-fophenyl)azo]benzenesulfonic acid disodium salt (C.I. 13015; Acid Yellow No. 9), 5-[(2,4-dinitrophenyl)amino]-2-phenyl-aminobenzenesulfonic acid sodium salt (C.I. 10385; Acid Orange No. 3), 4-[(2,4-dihydroxyphenyl)azo]benzenesulfonic acid monosodium salt (C.I. 14270; Acid Orange No. 6), 4-[(2-hydroxynaphth-1-yl) azo]benzenesulfonic acid sodium salt (C.I. 15510; Acid Orange No. 7), 4-[(2-hydroxynaphthalen-1-yl)azo]-3-methylbenzenesulfonic acid sodium salt (C.I. 15575; Acid Orange No. 8), 4-[(2,4-dihydroxy-3-[(2,4-dimethylphenyl)azo]phenyl)azo]benzenesulfonic acid sodium salt (C.I. 20170; Acid Orange No. 24), 3',6'-dihydroxy-4',5'-diiodospiro[isobenzofuran-1(3H)-9'-(9H)xanthen]-3-one (C.I. 45425; D&C Orange No. 10), 4-hydroxy-3-[(4-sulfonaphth-1-yl)azo]-1-naphthalenesulfonic acid disodium salt (C.I. 14720; Acid Red No. 14), 4-hydroxy-3-[(2-methoxy-phenyl)azo]-1-napthalenesulfonic acid monosodium salt (C.I. 14710; Acid Red No. 4), 6-hydroxy-5-[(4-sulfonaphth-1-yl)azo]-2,4-naphthalenedisulfonic acid trisodium salt (C.I. 16255; Ponceau 4R; Acid Red No. 18), 3-hydroxy-4-[(4-sulfonaphth-1-yl)azo]-2,7-naphthalenedisulfonic acid trisodium salt (C.I. 16185; Acid Red No. 27), 8-amino-1-hydroxy-2-(phenylazo)-3,6-naphthalenedisulfonic acid disodium salt (C.I. 17200; Acid Red No. 33), 5-(acetylamino)-4-hydroxy-3-[(2-methylphenyl) azo]-2,7-naphthalenedisulfonic acid disodium salt (C.I. 18065; Acid Red No. 35), 2-(3-hydroxy-2,4,5,7-tetraiododibenzopyran-6-on-9-yl)benzoic acid disodium salt (C.I. 45430; Acid Red No. 51), N-[6-(diethylamino)-9-(2,4-disulfophenyl)-3H-xanthen-3-ylidene]-N-ethylethanammonium hydroxide, inner salt, sodium salt (C.I. 45100; Acid Red No. 52), 8-{[4-(phenylazo)phenyl]azo}-7-naphthol-1,3-disulfonic acid disodium salt (C.I. 27290; Acid Red No. 73), 2',4',5',7'-tetrabromo-3',6'-dihydroxyspiro{isobenzofuran-1(3H), 9'[9H]-xanthen}3-one disodium salt (C.I. 45380; Acid Red No. 87), 2',4',5',7'-tetrabromo-4,5,6,7-tetrachloro-3',6'-dihydroxyspiro{isobenzofuran-1-(3H), 9'[9H]xanthen}-3-one disodium salt (C.I. 45410; Acid Red No. 92), 3',6'-dihydroxy-4',5'-diiodospiro[isobenzofuran-1(3H), 9'(9H)-xanthen]-3-one disodium salt (C.I. 45425; Acid Red No. 95), 2-hydroxy-3-[(2-hydroxynaphth-1-yl)azo]-5-nitrobenzenesulfonic acid monosodium salt (C.I. 15685; Acid Red No. 184), (2-sulfophenyl)di[4-(ethyl((4-sulfophenyl)methyl) amino)phenyl]carbenium disodium salt, betaine (C.I. 42090; Acid Blue No. 9; FD&C Blue No. 1), 3-hydroxy-4-[(4-methyl-2-sulfophenyl)azo]-2-naphthalenecarboxylic acid disodium salt (C.I. 15850; D&C Red No. 6), 6-hydroxy-5-[(2-methoxy-5-methyl-4-sulfophenyl)azo]-2-naphthalenesulfonic acid disodium salt (C.I. 16035; FD&C Red 40), 1,4-bis[(2-sulfo-4-methylphenyl)amino]-9,10-anthraquinone disodium salt (C.I. 61570; Acid Green No. 25), bis[4-(dimethylamino)phenyl]-(3,7-disulfo-2-hydroxynaphth-1-yl)carbenium inner salt, monosodium salt (C.I. 44090; Food Green No. 1; Acid Green No. 50), bis[4-(diethylamino)phenyl](2,4-disulfophenyl)carbenium inner salt, sodium salt (2:1) (C.I. 42045; Food Blue No. 3; Acid Blue No. 1), bis[4-(diethylamino)phenyl](5-hydroxy-2,4-disulfophenyl)-carbenium inner salt, calcium salt (2:1) (C.I. 42051; Acid Blue No. 3), 1-amino-4-(cyclohexylamino)-9,10 anthraquinone-2-sulfonic acid sodium salt (C.I. 62045; Acid Blue No. 62), 3,3-bis(3,5-dibromo-4-hydroxyphenyl)-4,5,6,7-tetrabromo-2,1(3H)-benzoxathiol-1,1-dioxide, 1-amino-4-(phenylamino)-9,10-anthraquinone-2-sulfonic acid (C.I. 62055; Acid Blue No. 25), 2-(1,3-dihydro-3-keto-5-sulfo-2H-indol-2-ylidene)-2,3-dihydro-3-keto-1H-indol-5-sulfonic acid disodium salt (C.I. 73015); Acid Blue No. 74), 9-(2-carboxyphenyl)-3-[(2-methylphenyl)amino]-6-[(2-methyl-4-sulfophenyl)amino]xanthylium inner salt, monosodium salt (C.I. 45190; Acid Violet No. 9), 1-hydroxy-4-[(4-methyl-2-sulfophenyl)amino]-9,10-anthraquinone sodium salt (C.I. 60730; D&C Violet No. 2; Acid Violet No. 43), bis{3-nitro-4-[(4-phenylamino)-3-sulfophenylamino] phenyl}sulfone (C.I. 10410; Acid Brown No. 13), 5-amino-4-hydroxy-6-[(4-nitrophenyl)azo]-3-(phenylazo)-2,7-naphthalenedisulfonic acid disodium salt (C.I. 20470; Acid Black No. 1), 3-hydroxy-4-[(2-hydroxynaphth-1-yl)azo]-7-nitro-1-naphthalenesulfonic acid chromium complex (3:2) (C.I. 15711; Acid Black No. 52), 3-[(2,4-dimethyl-5-sulfophenyl) azo]-4-hydroxy-1-naphthalenesulfonic acid disodium salt (C.I. 14700; Food Red No. 1; Ponceau SX; FD&C Red No. 4), 4-(acetylamino)-5-hydroxy-6-[(7-sulfo-4-[(4-sulfophenyl) azo]naphth-1-yl)azo]-1,7-naphthalenedi-sulfonic acid tetrasodium salt (C.I. 28440; Food Black No. 1) and 3-hydroxy-4-(3-methyl-5-keto-1-phenyl-4,5-dihydro-1H-pyrazol-4-ylazo)naphthalene-1-sulfonic acid sodium salt, chromium complex (Acid Red No. 195).

The colorant of the invention can contain the afore-said direct dyes in a total amount from about 0.01 to 4 weight percent, the total amount of dyes in the colorant of the invention preferably being from about 0.01 to 10 weight percent and particularly from 0.1 to 8 weight percent.

Naturally, it is also possible to add to the colorant of the invention oxidation dye precursors (developers and couplers), for example o,p,m-phenylenediamines, o,p,m-aminophenols, diphenols or 4,5-diaminopyrazoles, as well as suitable oxidants (particularly hydrogen peroxide and the adducts thereof.

The colorant can contain each of these additional developers and couplers in a total amount of about 0.01 to 20 weight percent, preferably from 0.1 to 10 weight percent and particularly from 0.1 to 5 weight percent.

The colorant of the invention can be in the form of, for example, a solution, particularly an aqueous or aqueous-alcoholic solution, or a cream, a gel, a surfactant-containing foaming solution (shampoo, aerosol), an emulsion or some other water-containing carrier suitable for use on hair. The colorant of the invention can also be in the form of pellets, granulate or powder which before use is dissolved in an aqueous preparation, for example water or an aqueous oxidant preparation. The composition of these agents consists of a mixture of the dye component and the additives usually employed for such preparations.

Common additives to solutions, creams, emulsions and gels are, for example, solvents such as water, the lower monohydric or polyhydric aliphatic alcohols, the esters and ethers thereof, for example alkanols, particularly those with 1 to 4 carbon atoms, for example ethanol, propanol, isopropanol, butanol, isobutanol, dihydric and trihydric alcohols, particularly those with 2 to 6 carbon atoms, for example ethylene glycol, propylene glycol, 1,3-propanediol, 1,4-butanediol, 1,5-pentanediol, 1,6-hexanediol, 1,2,6-hexanetriol, glycerol, diethylene glycol, dipropylene glycol, polyalkylene glycols such as triethylene glycol, polyethylene glycol, tripropylene glycol, polypropylene glycol, the lower alkyl ethers of polyhydric alcohol such as ethylene glycol monomethyl ether, ethylene glycol monoethyl ether, ethylene glycol monopropyl ether, ethylene glycol monobutyl ether, diethylene glycol monomethyl ether, diethylene glycol monoethyl ether, triethylene glycol monomethyl ether and triethylene glycol monoethyl ether, ketones and ketoalcohols, particularly those with 3 to 7 carbon atoms, for example acetone, methyl ethyl ketone, diethyl ketone, methyl isobutyl ketone, methyl phenyl ketone, cyclopentanone, cyclohexanone, diacetonealcohol, ethers, for example dibutyl ether, tetrahydrofuran, dioxane, diisopropyl ether, esters, for example ethyl formate, methyl formate, methyl acetate, ethyl acetate, propyl acetate, butyl acetate, phenyl acetate, ethylene glycol monoethyl ether acetate and hydroxyethyl acetate, amides, for example dimethylformamide and dimethylacetamide, N-methylpyrrolidone as well as urea, tetramethylurea and thiodiglycol.

Moreover, the colorant of the invention can contain wetting agents or emulsifiers from the class of anionic, cationic, amphoteric, nonionic or zwitterionic surface-active substances, for example fatty alcohol sulfates, ethoxylated fatty alcohol sulfates, alkylsulfonates, alkylbenzenesulfonates, α-olefinsylfonates, alkyltrimethylammonium salts, alkylbetaines, ethoxylated fatty alcohols, ethoxylated nonylphenols, fatty alkanolamides, ethoxylated fatty esters, fatty alcohol polyglycol ether sulfates, alkylpolyglucosides, thickeners such as the higher fatty alcohols, starch, cellulose derivatives, vaselines, paraffin oil, fatty acids and other fat constituents in emulsified form, water-soluble polymeric thickeners such as the natural gums, guar gum, xanthan gum, carob bean flour, pectin, dextran, agar, amylose, amylopectin, dextrins, clays or fully synthetic hydrocolloids, for example polyvinyl alcohol, as well as hair-care agents such as lanolin derivatives, cholesterol, pantothenic acid, water-soluble cationic polymers, protein derivatives, provitamins, vitamins, plant extracts, sugar and betaine, auxiliary agents such as moisturizers, electrolytes, antioxidants, fatty amides, sequestering agents, film-forming agents and preservatives. In addition to water, a water-soluble organic solvent or a mixture of such solvents and a water/solvent mixture can be used.

The said constituents are used in amounts normally employed for such purposes, for example the wetting agents and emulsifiers at a concentration from about 0.1 to 30 wt. %, the thickeners in an amount from about 0.1 to 30 wt. % and the hair-care agents at a concentration from about 0.1 to 5 wt. %.

The colorant of the invention has a pH from about 3 to 11 and preferably from about 3 to 10. Both organic and inorganic acids or bases are suitable for adjusting the pH according to the invention. Suitable acids are, in particular, the following: α-hydroxycarboxylic acids, for example glycolic, lactic, tartaric, citric and malic acid; ascorbic acid; gluconolactone, acetic acid, hydrochloric acid and phosphoric acid as well as mixtures of said acids. Suitable bases are, in particular, sodium carbonate, sodium hydrogen carbonate, potassium carbonate, potassium hydrogen carbonate, sodium phosphate, borax ($Na_2B_4O_7 \times 10H_2O$), disodium hydrogen phosphate, sodium hydroxide, potassium hydroxide, ammonia and other organic amines such as monoethanolamine, diethanolamine, triethanolamine, N-methyl-N-ethanolamine, N-methyl-N,N-diethanolamine, 2-(2-hydroxyethoxy)-ethanolamine, di-2-(2-hydroxyethoxy)ethanamine and tri-2-(2-hydroxyethoxy)ethanamine. An alkaline pH is preferably obtained by adjustment with ammonia and/or monoethanolamine.

As a rule, the colorant of the invention is used by applying to the hair an amount thereof sufficient for hair dyeing namely about 30 to 120 grams depending on the length of the hair. The colorant is then allowed to act on the hair at about 15 to 50° C. and preferably at 30 to 40° C. for about 1 to 60 minutes and preferably for 5 to 30 minutes after which the hair is thoroughly rinsed with water, optionally washed with a shampoo, and then dried.

The afore-described colorant can also contain natural or synthetic polymers or modified polymer of natural origin commonly used in cosmetic agents and whereby the hair is fixed at the same time as it is colored. Such agents are generally referred to as tinting fixatives or dye fixatives.

Synthetic polymers known to be suitable for this purpose in the cosmetic field are, for example, polyvinylpyrrolidone, polyvinyl acetate, polyvinyl alcohol and polyacrylic compounds such as polyacrylic acid and polymethacrylic acid, basic polymers of the esters of polyacrylic acid or of polymethacrylic acid and aminoalcohols, for example the salts or quaternization products thereof, polyacrylonitrile, polyvinyl acetates and the copolymers of such compounds, for example polyvinylpyrrolidone-vinyl acetate. Suitable natural polymers or modified natural polymers are, for example, chitosan (deacetylated chitin) and chitosan derivatives.

The agent of the invention contains the afore-said polymers in an amount usually employed for such agents, particularly in an amount from about 1 to 5 wt. %. The pH of the tinting fixative or dye fixative of the invention is preferably about 4 to 10.

The hair colorant with additional fixative action is applied in the known and usual manner by moistening the hair with the fixative, arranging the hair into a hairdo and then drying. The colorants of the invention make it possible to achieve an outstanding, uniform, intense and durable red to violet coloration of keratin fibers, for example of human hair, wool and furs, showing excellent light stability and resistance to perspiration.

Some of the dyes of formula (I) are in and of themselves known. They can be prepared by methods analogous to the known methods of preparation, for example via azo coupling of 2-aminothiazole derivatives with indol derivatives followed by quaternization.

The following examples will explain the subject matter of the invention in greater detail without limiting it to these examples.

EXAMPLES

Coloring Examples 1 to 9

| | |
|---|---|
| 2.5 mmol | of compound of formula (I) as per Table 1 |
| 12.5 g | of ethanol |
| 10.0 g | of cetyltrimethylammonium chloride |
| to 100.0 g | water, demineralized |

When necessary, the coloring solution was adjusted to the desired pH by addition of ammonia or citric acid.

The hair was colored by applying to it an amount of colorant sufficient for hair dyeing and spreading it uniformly with a brush. After an exposure time of 30 min at 40° C., the hair was rinsed with lukewarm water, washed with a shampoo, rinsed with lukewarm water and then dried.

The coloring results are summarized in the following Table 1.

Coloring Examples 10 to 15

| | |
|---|---|
| 0.625 mmol | of compound of formula (I) as per Table 2 |
| 0.625 mmol | of cationic dye as per Table 2 |
| 5.0 g | of ethanol |
| 4.0 g | of decylglucoside |
| 0.2 g | of ethylenediaminetetraacetic acid disodium salt |
| to 100.0 g | water, demineralized |

When necessary, the coloring solution was adjusted to the desired pH by addition of ammonia or citric acid.

The hair was colored by applying to it an amount of colorant sufficient for hair dyeing and spreading it uniformly with a brush. After an exposure time of 30 min at 40° C., the hair was rinsed with lukewarm water, washed with a shampoo, rinsed with lukewarm water and then dried.

The amounts of the dyes used and the coloring results are summarized in the following Table 2.

TABLE 1

| Example | Compound of Formula (I) | pH of Colorant | Color After Dyeing | Color Values After Dyeing |
|---|---|---|---|---|
| 1 | 3-methyl-2-[(1-methyl-2-phenyl-1H-indol-3-yl)azo]thazolium monomethylsulfate | 6.2 | red | L = 29.61<br>a = 47.13<br>b = 19.96 |
| 2 | 3,5-dimethyl-2-[(1-methyl-2-phenyl-1H-indol-3-yl)azo]thiazolium monomethylsulfate | 6.6 | red-violet | L = 31.15<br>a = 46.96<br>b = 15.86 |
| 3 | 3,4-dimethyl-2-[(1-methyl-2-phenyl-1H-indol-3-yl)azo]thiazolium monomethylsulfate | 6.5 | red-violet | L = 27.93<br>a = 42.70<br>b = 14.21 |
| 4 | 3,4,5-trimethyl-2-[(1-methyl-2-phenyl-1H-indol-3-yl)azo]thiazolium monomethylsulfate | 6.6 | violet | L = 25.42<br>a = 37.65<br>b = 6.95 |
| 5 | 5-bromo-3-methyl-2-[(1-methyl-2-phenyl-1H-indol-3-yl)azo]thiazolium monomethylsulfate | 5.9 | violet-pink | L = 35.87<br>a = 46.89<br>b = 4.09 |
| 6 | 5-methoxy-3-methyl-2-[(1-methyl-2-phenyl-1H-indol-3-yl)azo]thiazolium monomethylsulfate | 7.3 | violet-eggplant | L = 24.17<br>a = 36.57<br>b = 1.55 |
| 7 | 3-methyl-2-[(2-phenyl-1H-indol-3-yl)azo]thiazolium monomethylsulfate | 3.2 | red | L = 42.66<br>a = 36.46<br>b = 16.15 |
| 8 | 3-methoxy-2-[(2-phenyl-1H-indol-3-yl)azo]thiazolium monomethylsulfate | 3.1 | pink | L = 61.06<br>a = 25.74<br>b = 8.08 |
| 9 | 3-methyl-2-[(1,2-diphenyl-1H-indol-3-yl)azo]thiazolium monomethylsulfate | 6.2 | red | L = 28.51<br>a = 45.89<br>b = 17.46 |

TABLE 2

| Example | Compound of Formula (I)/Cationic Dye | pH of Colorant | Color After Dyeing | Color Values After Dyeing |
|---|---|---|---|---|
| 10 | 3-methyl-2-[(1-methyl-2-phenyl-1H-indol-3-yl)azo]thiazolium monomethylsulfate (0.27 g) Basic Brown 17 (0.25 g) | 7.3 | red-orange | L = 29.07 a = 42.07 b = 19.43 |
| 11 | 3-methyl-2-[(1-methyl-2-phenyl-1H-indol-3-yl)azo]thiazolium monomethylsulfate (0.27 g) Basic Brown No. 16 (0.22 g) | 7.2 | brown-red | L = 24.32 a = 25.51 b = 12.99 |
| 12 | 3-methyl-2-[(1-methyl-2-phenyl-1H-indol-3-yl)azo]thiazolium monomethylsulfate (0.27 g) Basic Yellow No. 57 (0.23 g) | 7.1 | red-orange | L = 31.10 a = 46.60 b = 23.20 |
| 13 | 3-methyl-2-[(1-methyl-2-phenyl-1H-indol-3-yl)azo]thiazolium monomethylsulfate (0.27 g) Basic Blue No. 99 (0.28 g) | 7.1 | brown-violet | L = 20.73 a = 11.10 b = 4.80 |
| 14 | 3-methyl-2-[(1-methyl-2-phenyl-1H-indol-3-yl)azo]thiazolium monomethylsulfate (0.27 g) Basic Violet No. 2 (0.23 g) | 7.3 | violet-red | L = 26.46 a = 43.82 b = 15.49 |
| 15 | 3-methyl-2-[(1-methyl-2-phenyl-1H-indol-3-yl)azo]thiazolium monomethylsulfate (0.27 g) Basic Brown 17 (0.25 g) Basic Yellow No. 57 (0.23 g) Basic Blue No. 99 (0.28 g) | 7.1 | brown | L = 25.22 a = 17.27 b = 10.17 |

Coloring Example 16

| | | |
|---|---|---|
| 2.5 | mmol | of dye of formula (I) |
| 5.0 | g | of ethanol |
| 4.0 | g | of decylglucoside |
| 0.2 | g | of ethylenediaminetetraacetic acid disodium salt |
| to 100.0 | g | water, demineralized |

When necessary, the coloring solution was adjusted to the desired pH by addition of ammonia or citric acid.

The hair was colored by applying to it an amount of colorant sufficient for hair dyeing and spreading it uniformly with a brush. After an exposure time of 30 min at 40° C., the hair was rinsed with lukewarm water, washed with a shampoo, rinsed with lukewarm water and then dried.

The coloring results are summarized in the following Table 3.

TABLE 3

| Example | Compound of Formula (I) | pH of Colorant | Color After Dyeing | Color Values After Dyeing |
|---|---|---|---|---|
| 16 | 3-methyl-2-[(1-methyl-2-phenyl-1H-indol-3-yl)azo]thiazolium monomethylsulfate | 7.5 | red | L = 31.7 a = 48.8 b = 23.8 |

Coloring Example 17

| | | |
|---|---|---|
| 2.5 | mmol | of dye of formula (I) |
| 5.0 | g | of ethanol |
| 7.5 | g | of tegobetaine |
| 100.0 | g | water, demineralized |

When necessary, the coloring solution was adjusted to the desired pH by addition of ammonia.

The hair was colored by applying to it an amount of colorant sufficient for hair dyeing and spreading it uniformly with a brush. After an exposure time of 30 min at 40° C., the hair was rinsed with lukewarm water, washed with a shampoo, rinsed with lukewarm water and then dried.

The coloring results are summarized in the following Table 4.

TABLE 4

| Example | Compound of Formula (I) | pH of Colorant | Color After Dyeing | Color Values After Dyeing |
|---|---|---|---|---|
| 17 | 3-methyl-2-[(1-methyl-2-phenyl-1H-indol-3-yl)azo]thiazolium monomethylsulfate | 9.7 | red | L = 29.97 a = 42.76 b = 19.45 |

Coloring Example 18

| | | |
|---|---|---|
| 2.5 | mmol | of dye of formula (I) |
| 5.0 | g | of ethanol |
| 7.5 | g | of lauryl ether sulfate, 28% in water |
| to 100.0 | g | water, demineralized |

When necessary, the coloring solution was adjusted to the desired pH by addition of ammonia.

The hair was colored by applying to it an amount of colorant sufficient for hair dyeing and spreading it uniformly with a brush. After an exposure time of 30 min at 40° C., the hair was rinsed with lukewarm water, washed with a shampoo, rinsed with lukewarm water and then dried.

The coloring results are summarized in the following Table 5.

TABLE 5

| Example | Compound of Formula (I) | pH of Colorant | Color After Dyeing | Color Values After Dyeing |
|---|---|---|---|---|
| 18 | 3-methyl-2-[(1-methyl-2-phenyl-1H-indol-3-yl)azo]thiazolium monomethylsulfate | 9.0 | pale red | L = 50.44<br>a = 42.03<br>b = 18.67 |

In the foregoing examples, the indicated L*a*b* color values were determined with the aid of a Chromameter II color-measuring instrument supplied by Minolta. Here the L-values stand for brightness (namely the lower the L-value, the higher is the color intensity), whereas the a-value is a measure of the red content of the color (namely the higher the a-value, the higher is the red content). The b-value is a measure of the blue content of the color, namely the more negative the b-value the higher is the blue content.

Unless otherwise indicated, all percentages in the present patent application are by weight.

What is claimed is:

1. An agent for coloring keratin fibers comprising:
water;
optionally at least one monohydric alcohol with 1 to 4 carbon atoms;
optionally at least one dihydric or trihydric alcohol with 2 to 6 carbon atoms;
at least one cosmetic additive selected from the group consisting of anionic surfactants, cationic surfactants, amphoteric surfactants, nonionic surfactants, zwitterionic surfactants, thickeners, hair-care agents, moisturizers, electrolytes, antioxidants, fatty amides, sequestering agents, film-forming agents, and preservatives; and
at least one indolylthiazoliumazo dye of general formula (I)

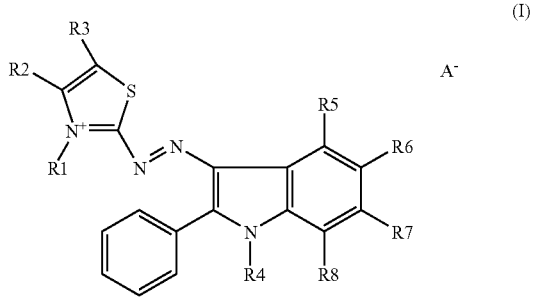

wherein
R1 is a saturated or unsaturated $(C_1-C_{12})$-alkyl group, a halogen atom substituted $(C_1-C_{12})$-alkyl group, a hydroxy-$(C_1-C_{12})$-alkyl group, a $(C_1-C_6)$-alkoxy-$(C_1-C_{12})$-alkyl group, an amino-$(C_1-C_{12})$-alkyl group, a $(C_1-C_6)$-alkylamino-$(C_1-C_{12})$-alkyl group, a di$(C_1-C_6)$-alkyl-amino-$(C_1-C_{12})$-alkyl group, a cyano-$(C_1-C_{12})$-alkyl group, a substituted or unsubstituted phenyl group or a substituted or unsubstituted benzyl group;
R2 and R3 can be equal or different and independently of each other stand for hydrogen, a halogen atom, a saturated or unsaturated $(C_1-C_{12})$-alkyl group, a $(C_1-C_{12})$-alkoxy group, a nitro group, an amino group, a $(C_1-C_{12})$-alkylamino group, a di$(C_1-C_{12})$-alkylamino group, a $(C_1-C_{12})$-hydroxyalkylamino group, a di$(C_1-C_{12})$-hydroxyalkylamino group, a substituted or unsubstituted phenyl group or a substituted or unsubstituted heteroaryl group;
R4 stands for hydrogen, a saturated or unsaturated $(C_1-C_{12})$-alkyl group, a halogen atom substituted $(C_1-C_{12})$-alkyl group, a hydroxy-$(C_1-C_{12})$-alkyl group, $(C_1-C_6)$-alkoxy-$(C_1-C_{12})$-alky group, an amino-$(C_1-C_{12})$-alkyl group, a $(C_1-C_6)$-alkylamino-$(C_1-C_{12})$-alkyl group, a di$(C_{1-6})$-alkylamino-$(C_{1-C12})$-alkyl group, a cyano-$(C_1-C_{12})$-alkyl group, a substituted or unsubstituted phenyl group, a substituted or unsubstituted benzyl group or a substituted or unsubstituted heteroaryl group;
R5, R6, R7 and R8 can be equal or different and independently of each other stand for hydrogen, a halogen atom, a saturated or unsaturated $(C_1-C_{12})$-alkyl group, a hydroxyl group, a $(C_1-C_{12})$-alkoxy group, a nitro group, an amino group, a $(C_1-C_{12})$-alkylamino group or a di$(C_1-C_{12})$-alkylamino group, and
$A^-$ stands for an anion of an organic or inorganic acid.

2. Agent An agent as defined in claim 1, wherein R1 stands for a saturated or unsaturated $(C_1-C_{12})$-alkyl group and R4 stands for hydrogen, a saturated or unsaturated $(C_1-C_{12})$-alkyl group or a substituted or unsubstituted phenyl group.

3. An agent as defined in claim 2, wherein R1 stands for a saturated $(C_1-C_{12})$-alkyl group and R4 stands for hydrogen, a saturated $(C_1-C_{12})$-alkyl group or an un-substituted phenyl group.

4. An agent as defined in claim 1, wherein $A^-$ stands for a chloride, bromide, iodide, hydrogen sulfate, sulfate, toluenesulfonate, benzenesulfonate, monomethylsulfate, hexafluorophosphate, hexafluoroantimonate, tetrafluororborate, tetraphenylborate, formate, acetate or propionate anion.

5. An agent as defined in claim 1, wherein the compound of formula (I) is selected from among 3-methyl-2-[(1-methyl-2-phenyl-1H-indol-3-yl)azo]thiazolium chloride, 3-methyl-2-[(1-methyl-2-phenyl-1H-indol-3-yl)azo]thiazolium bromide, 3-methyl-2-[(1-methyl-2-phenyl-1H-indol-3-yl)azo]thiazolium monomethylsulfate, 3,4-dimethyl-2-[(1-methyl-2-phenyl-1H-indol-3-yl)azo]thiazolium chloride, 3,4-dimethyl-2-[(1-methyl-2-phenyl-1H-indol-3-yl)azo]thiazolium bromide, 3,4-dimethyl-2-[(1-methyl-2-phenyl-1H-indol-3-yl)azo]thiazolium monomethylsulfate, 3,5-dimethyl-2-[(1-methyl-2-phenyl-1H-indol-3-yl)azo]thiazolium chloride, 3,5-dimethyl-2-[(1-methyl-2-phenyl-1H-indol-3-yl)-azo]-thiazolium bromide, 3,5-dimethyl-2-[(1-methyl-2-phenyl-1H-indol-3-yl)azo]thiazolium monomethylsulfate, 3,4,5-trimethyl-2-[(1-methyl-2-phenyl-1H-indol-3-yl)azo]thiazolium chloride, 3,4,5-trimethyl-2-[(1-methyl-2-phenyl-1H-indol-3-yl)azo]thiazolium bromide, 3,4,5-trimethyl-2-[(1-methyl-2-phenyl-1H-indol-3-yl)azo]thiazolium monomethylsulfate, 5-bromo-3-methyl-2-[(1-methyl-2-phenyl-1H-indol-3-yl)azo]thiazolium chloride, 5-bromo-3-methyl-2-[(1-methyl-2-phenyl-1H-indol-3-yl)azo]thiazolium bromide, 5-bromo-3-methyl-2-[(1-methyl-2-phenyl-1H-indol-3-yl)azo]thiazolium monomethylsulfate, 5-methoxy-3-methyl-2-[(1-methyl-2-phenyl-1H-indol-3-yl)azo]thiazolium chloride, 5-methoxy-3-methyl-2-[(1-methyl-2-phenyl-1H-indol-3-yl)azo]thiazolium bromide, 5-methoxy-3-methyl-2-[(1-methyl-2-phenyl-1H-indol-3-yl)azo]thiazolium monomethylsulfate, 3-methyl-2-[(2-phenyl-1H-indol-3-yl)azo]thiazolium chloride, 3-methyl-2-[(2-phenyl-1H-indol-3-yl)azo]thiazolium bromide, 3-methyl-2-[(2-phenyl-1H-indol-3-yl)azo]thiazolium monomethylsulfate, 3,4-dimethyl-2-[(2-phenyl-1H -indol-3-yl)azo]thiazolium chloride, 3,4-dimethyl-2-[(2-phenyl-1H-indol-3-yl)azo]-thiazolium bromide, 3,4-dimethyl-2-[(2- phenyl-1H-indol-3-yl)azo]thiazolium monomethylsulfate, 3,5-dimethyl-2-[(2-phenyl-1H-indol-3-yl)azo]thiazolium chloride, 3,5-dimethyl-2-[(2-phenyl-1H-indol-3-yl)azo]thiazolium bromide, 3,5-dimethyl-2-[(2-phenyl-1H-indol-3-yl)azo]thiazolium monomethylsulfate, 3,4,5-trimethyl-2-[(2-phenyl-1H-indol-3-yl)azo]thiazolium chloride, 3,4,5-trimethyl-2-[(2-phenyl-1H-indol-3-yl)azo]thiazolium bromide, 3,4,5-trimethyl2-[(2-phenyl-1H-indol-3-yl)azo]thiazolium monomethylsulfate, 5-bromo-3-methyl-2-[(2-phenyl-1H-indol-3-yl)azo]thiazolium chloride, 5-bromo-3-methyl-2-[(2-phenyl-1H-indol-3-yl)azo]thiazolium bromide, 5-bromo-3-methyl-2-[(2-phenyl-1H-indol-3-yl)azo]thiazolium monomethylsulfate, 5-methoxy-3-methyl-2-[(2-phenyl-1H-indol-3-yl)azo]thiazolium chloride, 5-methoxy-3-methyl-2-[(2-phenyl-1H-indol-3-yl)azo]thiazolium bromide, 5-methoxy-3-methyl-2-[(2-phenyl-1H-indol-3-yl)azo]thiazolium monomethylsulfate, 3-methyl-2-[(1,2-diphenyl-1H-indol-3-yl)azo]thiazolium chloride, 3-methyl-2-[(1,2-diphenyl-1H-indol-3-yl)azo]-thiazolium bromide, 3-methyl-2-[(1,2-diphenyl-1H-indol-3-yl)azo]thiazolium monomethyl-sulfate, 3,4-dimethyl-2-[(1,2-diphenyl-1H-indol-3-yl)azo]thiazolium chloride, 3,4-dimethyl-2-[(1,2-diphenyl-1H-indol-3-yl)azo]thiazolium bromide, 3,4-dimethyl-2-[(1,2-diphenyl-1H-indol-3-yl)azo]thiazolium monomethylsulfate, 3, 5-dimethyl-2-[(1,2-diphenyl-1H-indol-3-yl) -azo]thiazolium chloride, 3,5-dimethyl-2-[(1,2-diphenyl-1H-indol-3-yl)azo]thiazolium bromide, 3,5-dimethyl-2-[(1,2-diphenyl-1H-indol-3-yl)azo]thiazolium monomethylsulfate, 3,4,5-trimethyl-2-[(1,2-diphenyl-1H-indol-3-yl)azo]thiazolium chloride, 3,4,5-trimethyl-2-[(1,2-diphenyl-1H-indol-3-yl)azo]thiazolium bromide, 3,4,5-trimethyl-2-[(1,2-diphenyl-1H-indol-3-yl)azo]thiazolium monomethylsulfate, 5-bromo-3-methyl-2-[(1,2-diphenyl-1H-indol-3-yl)azo]thiazolium chloride, 5-bromo-3-methyl-2-[(1,2-diphenyl-1H-indol-3-yl)azo]thiazolium bromide, 5-bromo-3-methyl-2-[(1,2-diphenyl-1H-indol-3-yl)azo] thiazolium monomethylsulfate, 5-methoxy-3-methyl-2-[(1,2-diphenyl-1H-indol-3-yl)azo]thiazolium chloride, 5-methoxy-3-methyl-2-[(1,2-diphenyl-1H-indol-3-yl)azo] thiazolium bromide and 5-methoxy-3-methyl-2-[(1,2-diphenyl-1H-indol-3-yl)azo]thiazolium monomethylsulfate.

6. An agent as defined in claim 1, wherein the agent contains the compound of formula (1) in an amount from 0.01 to 10 weight percent.

7. An agent as defined in claim 1, wherein the agent contains at least one additional direct dye.

8. An agent as defined in claim 7, wherein the agent contains the additional direct dye in a total amount from 0.01 to 4 weight percent.

9. An agent as defined in claim 1, wherein the agent additionally contains oxidation dye precursors and before use is mixed with an oxidant.

10. An agent as defined in claim 1, wherein the agent has a pH ranging from 3 to 10.

11. An agent as defined in claim 1, wherein the agent contains at least one natural polymer, synthetic polymer or modified polymer of natural origin commonly used in cosmetic agents and is in the form of a tinting fixative or dye fixative.

12. An agent as defined in claim 1, wherein the agent is a hair colorant.

* * * * *